United States Patent [19]
Lu

[11] Patent Number: 5,885,962
[45] Date of Patent: Mar. 23, 1999

[54] STEM CELL FACTOR ANALOG COMPOSITIONS AND METHOD

[75] Inventor: Hsieng Lu, Thousand Oaks, Calif.

[73] Assignee: Amgen Inc., Thousand Oaks, Calif.

[21] Appl. No.: 628,428

[22] Filed: Apr. 5, 1996

[51] Int. Cl.⁶ .............................. A61K 38/18; C07K 14/46
[52] U.S. Cl. .......................... 514/12; 530/350; 530/350.1; 530/399
[58] Field of Search ................................ 530/350, 350.1, 530/399; 514/2

[56] References Cited

FOREIGN PATENT DOCUMENTS

| | | |
|---|---|---|
| 0676470 A | 10/1985 | European Pat. Off. . |
| 2258234 | 2/1993 | United Kingdom . |
| WO 83/04053 | 11/1983 | WIPO . |
| WO 91/05795 | 2/1991 | WIPO . |
| WO 92/03459 | 5/1992 | WIPO . |
| WO 92/00376 | 9/1992 | WIPO . |
| WO 9526199 | 5/1995 | WIPO . |

OTHER PUBLICATIONS

Langley K E; Mendiaz E A; Liu N; Narhi L O; Zeni L; Parseghian C M; Clogston C L; Leslie I; Pope J A; Lu H S; et al. Properties of variant forms of human stem cell factor recombinantly expressed in *Escherichia coli* . Archives of Biochemistry and Biophysi, May 1994.

Friedman A R; Ichhpurani A K; Brown D M; Hillman R M; Krabill L F; Martin R A; Zurcher–Nely H A; Guido D M. Degradation of growth hormone releasing factor analogs in neutral aqueous solution is related to deamidation of asparagine residues. Replacement, Jan. 1991.
White, Cell 63: 5–6 (1990).
Martin, et al., Cell 63: 203–211 (1990).
Langley, et al., Arch. Biochem. Biophys. 311: 55–61 (1994).
Lu, et al., Biochem. J. 305: 563–568 (1995).
Remingtons Pharmaceutical Sciences, 18th Ed. (1990), Mach Publishing Co., Easton, PA 18042, pp. 697–773.
Remingtons Pharmaceutical Sciences, 18th Ed. (1990), Mach Publishing Co., Easton, PA 18042, pp. 1435–1712.
Langley et al., Arch. Biochem. Biophys. 295: 21–28.
Smith, Kent et al., Current Protocols in Immunology (Coligan, et al., eds). Supplement 4 CPI, Unit 6, 17, pp. 6.17.1 to 6.17.11, John Wiley & Sons, New York (1992).
Zhang, et al., *Biology of Reproduction* 50:95–102 (1994).
Zhang, et al. *Biology of Reproduction* 50:95–102 (1994), see abstract, fig. 3.

*Primary Examiner*—Elizabeth Kemmerer
*Assistant Examiner*—David S. Romeo
*Attorney, Agent, or Firm*—Matthew W. Knight; Karol M. Pessin; Steven M. Odre

[57] ABSTRACT

The present invention relates to stem cell factor analog polypeptide compositions, and vectors, host cells, and processes for recombinant DNA production of the present stem cell factor analogs. Pharmaceutical compositions and methods of use are also disclosed.

3 Claims, 3 Drawing Sheets

FIG.1A

Amino Acid Sequence of Human SCF$^{1-248}$ with a Leader Sequence (Seq. ID No.9):

```
-25                    -20                                         
Met Lys Lys Thr Gln Thr Trp Ile Leu Thr Cys Ile Tyr Leu Gln

-10                                  1                          20
Leu Leu Leu Phe Asn Pro Leu Val Lys Thr Glu Gly Ile Cys Arg

10
Asn Arg Val Thr Asn Asn Val Lys Asp Val Thr Lys Leu Val Ala
                                        30
Asn Leu Pro Lys Asp Tyr Met Ile Thr Leu Lys Tyr Val Pro Gly
        40                                                   50
Met Asp Val Leu Pro Ser His Cys Trp Ile Ser Glu Met Val Val
                    60
Gln Leu Ser Asp Ser Leu Thr Asp Leu Leu Asp Lys Phe Ser Asn
            70                                              80
Ile Ser Glu Gly Leu Ser Asn Tyr Ser Ile Ile Asp Lys Leu Val
                        90
Asn Ile Val Asp Asp Leu Val Glu Cys Val Lys Glu Asn Ser Ser
                100                                         110
Lys Asp Leu Lys Lys Ser Phe Lys Ser Pro Glu Pro Arg Leu Phe
                            120
Thr Pro Glu Glu Phe Phe Arg Ile Phe Asn Arg Ser Ile Asp Ala
```

FIG.1B

```
                                                                    140
Phe Lys Asp Phe Val Val Als Ser Glu Thr Ser Asp Cys Val Val
        130
                                       150
Ser Ser Thr Leu Ser Pro Glu Lys Asp Ser Arg Val Ser Val Thr
                                                                    170
        160
Lys Pro Phe Met Leu Pro Pro Val Ala Ala Ser Ser Leu Arg Asn
                                       180
Asp Ser Ser Ser Asn Arg Lys Ala Lys Asn Pro Pro Gly Asp
                                                                    200
        190
Ser Ser Leu His Trp Ala Ala Met Ala Leu Pro Ala Leu Phe Ser
                                       210
Leu Ile Ile Gly Phe Ala Phe Gly Ala Leu Tyr Trp Lys Lys Arg
                                                                    230
        220
Gln Pro Ser Leu Thr Arg Ala Val Glu Asn Ile Gln Ile Asn Glu
                                       240
Glu Asp Asn Glu Ile Ser Met Leu Gln Glu Lys Glu Arg Glu Phe
        248
Gln Glu Val End
``` a: rhSCF, wild type
b: N10D, N11D variant
c: N10D variant
d: N10E variant

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
      ( A ) LENGTH: 501 base pairs
      ( B ) TYPE: nucleic acid
      ( C ) STRANDEDNESS: single
      ( D ) TOPOLOGY: linear    ( i i ) MOLECULE TYPE: cDNA    ( x i ) SEQUENCE DESCRIPTION: SEQ ID NO:1:

```
ATGGAAGGTA  TCTGCCGTAA  CCGTGTTACT  AACAACGTTA  AAGACGTTAC  TAAACTGGTT      60
GCTAACCTGC  CGAAAGACTA  CATGATCACC  CTGAAATACG  TTCCGGGTAT  GGACGTTCTG     120
CCGTCTCACT  GCTGGATCTC  TGAAATGGTT  GTTCAGCTGT  CTGACTCTCT  GACTGACCTG     180
CTGGACAAAT  TCTCTAACAT  CTCTGAAGGT  CTGTCTAACT  ACTCTATCAT  CGACAAACTG     240
GTTAACATCG  TTGACGACCT  GGTTGAATGC  GTTAAAGAAA  ACTCTTCTAA  AGACCTGAAA     300
AAATCTTTCA  AATCTCCGGA  ACCGCGTCTG  TTCACTCCGG  AAGAATTCTT  CCGTATCTTC     360
AACCGTTCCA  TCGACGCTTT  CAAAGACTTC  GTTGTTGCTT  CCGAAACCTC  CGACTGCGTT     420
```

GTTTCCTCCA CCCTGTCTCC GGAAAAAGAC TCCCGTGTTT CGGTTACCAA ACCGTTCATG    480

CTGCCGCCGG TTGCTGCTTA A    501

( 2 ) INFORMATION FOR SEQ ID NO:2:

( i ) SEQUENCE CHARACTERISTICS:
        ( A ) LENGTH: 166 amino acids
        ( B ) TYPE: amino acid
        ( C ) STRANDEDNESS: single
        ( D ) TOPOLOGY: linear     ( i i ) MOLECULE TYPE: protein     ( i x ) FEATURE:
        ( A ) NAME/KEY: Protein
        ( B ) LOCATION: 1..166
        ( D ) OTHER INFORMATION: /note= "Met sequence starts at -1
        on Sequence No. 2."

( x i ) SEQUENCE DESCRIPTION: SEQ ID NO:2:

```
Met Glu Gly Ile Cys Arg Asn Arg Val Thr Asn Asn Val Lys Asp Val
 1               5                  10                  15
Thr Lys Leu Val Ala Asn Leu Pro Lys Asp Tyr Met Ile Thr Leu Lys
             20                  25                  30
Tyr Val Pro Gly Met Asp Val Leu Pro Ser His Cys Trp Ile Ser Glu
         35                  40                  45
Met Val Val Gln Leu Ser Asp Ser Leu Thr Asp Leu Leu Asp Lys Phe
     50                  55                  60
Ser Asn Ile Ser Glu Gly Leu Ser Asn Tyr Ser Ile Ile Asp Lys Leu
 65                  70                  75                  80
Val Asn Ile Val Asp Asp Leu Val Glu Cys Val Lys Glu Asn Ser Ser
                 85                  90                  95
Lys Asp Leu Lys Lys Ser Phe Lys Ser Pro Glu Pro Arg Leu Phe Thr
                100                 105                 110
Pro Glu Glu Phe Phe Arg Ile Phe Asn Arg Ser Ile Asp Ala Phe Lys
            115                 120                 125
Asp Phe Val Val Ala Ser Glu Thr Ser Asp Cys Val Val Ser Ser Thr
        130                 135                 140
Leu Ser Pro Glu Lys Asp Ser Arg Val Ser Val Thr Lys Pro Phe Met
145                 150                 155                 160
Leu Pro Pro Val Ala Ala
                165
```

( 2 ) INFORMATION FOR SEQ ID NO:3:

( i ) SEQUENCE CHARACTERISTICS:
        ( A ) LENGTH: 512 base pairs
        ( B ) TYPE: nucleic acid
        ( C ) STRANDEDNESS: single
        ( D ) TOPOLOGY: linear     ( i i ) MOLECULE TYPE: cDNA     ( x i ) SEQUENCE DESCRIPTION: SEQ ID NO:3:

CATATGGAAG GTATCTGCAG GAATCGTGTG ACTGACAATG TAAAAGACGT CACTAAATTG    60

GTGGCAAATC TTCCAAAAGA CTACATGATA ACCCTCAAAT ATGTCCCCGG GATGGATGTT    120

TTGCCAAGTC ATTGTTGGAT AAGCGAGATG GTAGTACAAT TGTCAGACAG CTTGACTGAT    180

CTTCTGGACA AGTTTTCAAA TATTTCTGAA GGCTTGAGTA ATTATTCCAT CATAGACAAA    240

CTTGTGAATA TAGTGGATGA CCTTGTGGAG TGCGTGAAAG AAAACTCATC TAAGGATCTA    300

| | | |
|---|---|---|
| AAAAAATCAT TCAAGAGCCC AGAACCCAGG CTCTTTACTC CTGAAGAATT CTTCCGTATC | 360 |
| TTCAACCGTT CCATCGACGC TTTCAAAGAC TTCGTTGTTG CTTCCGAAAC CTCCGACTGC | 420 |
| GTTGTTTCCT CCACCCTGTC TCCGGAAAAA GACTCCCGTG TTTCGGTTAC CAAACCGTTC | 480 |
| ATGCTGCCGC CGGTTGCTGC TTAATAGGAT CC | 512 |

(2) INFORMATION FOR SEQ ID NO:4:

(i) SEQUENCE CHARACTERISTICS:
        (A) LENGTH: 512 base pairs
        (B) TYPE: nucleic acid
        (C) STRANDEDNESS: single
        (D) TOPOLOGY: linear     (ii) MOLECULE TYPE: cDNA     (xi) SEQUENCE DESCRIPTION: SEQ ID NO:4:

| | | |
|---|---|---|
| GTATACCTTC CATAGACGTC CTTAGCACAC TGACTGTTAC ATTTTCTGCA GTGATTTAAC | 60 |
| CACCGTTTAG AAGGTTTTCT GATGTACTAT TGGGAGTTTA TACAGGGGCC CTACCTACAA | 120 |
| AACGGTTCAG TAACAACCTA TTCGCTCTAC CATCATGTTA ACAGTCTGTC GAACTGACTA | 180 |
| GAAGACCTGT TCAAAAGTTT ATAAAGACTT CCGAACTCAT TAATAAGGTA GTATCTGTTT | 240 |
| GAACACTTAT ATCACCTACT GGAACACCTC ACGCACTTTC TTTTGAGTAG ATTCCTAGAT | 300 |
| TTTTTTAGTA AGTTCTCGGG TCTTGGGTCC GAGAAATGAG GACTTCTTAA GAAGGCATAG | 360 |
| AAGTTGGCAA GGTAGCTGCG AAAGTTTCTG AAGCAACAAC GAAGGCTTTG GAGGCTGACG | 420 |
| CAACAAAGGA GGTGGGACAG AGGCCTTTTT CTGAGGGCAC AAAGCCAATG GTTTGGCAAG | 480 |
| TACGACGGCG GCCAACGACG AATTATCCTA GG | 512 |

(2) INFORMATION FOR SEQ ID NO:5:

(i) SEQUENCE CHARACTERISTICS:
        (A) LENGTH: 166 amino acids
        (B) TYPE: amino acid
        (C) STRANDEDNESS: single
        (D) TOPOLOGY: linear     (ii) MOLECULE TYPE: protein     (ix) FEATURE:
        (A) NAME/KEY: Protein
        (B) LOCATION: 1..166
        (D) OTHER INFORMATION: /note= "Met sequence starts at -1
            on Sequence No. 5."

(xi) SEQUENCE DESCRIPTION: SEQ ID NO:5:

```
Met Glu Gly Ile Cys Arg Asn Arg Val Thr Asp Asn Val Lys Asp Val
 1               5                  10                  15

Thr Lys Leu Val Ala Asn Leu Pro Lys Asp Tyr Met Ile Thr Leu Lys
            20                  25                  30

Tyr Val Pro Gly Met Asp Val Leu Pro Ser His Cys Trp Ile Ser Glu
        35                  40                  45

Met Val Val Gln Leu Ser Asp Ser Leu Thr Asp Leu Leu Asp Lys Phe
    50                  55                  60

Ser Asn Ile Ser Glu Gly Leu Ser Asn Tyr Ser Ile Ile Asp Lys Leu
65                  70                  75                  80

Val Asn Ile Val Asp Asp Leu Val Glu Cys Val Lys Glu Asn Ser Ser
                85                  90                  95

Lys Asp Leu Lys Lys Ser Phe Lys Ser Pro Glu Pro Arg Leu Phe Thr
            100                 105                 110

Pro Glu Glu Phe Phe Arg Ile Phe Asn Arg Ser Ile Asp Ala Phe Lys
```

|     | 115 |     |     |     | 120 |     |     |     | 125 |     |     |     |     |
| --- | --- | --- | --- | --- | --- | --- | --- | --- | --- | --- | --- | --- | --- |
| Asp | Phe | Val | Val | Ala | Ser | Glu | Thr | Ser | Asp | Cys | Val | Ser | Ser | Thr |
|     | 130 |     |     |     |     | 135 |     |     |     | 140 |     |     |     |
| Leu | Ser | Pro | Glu | Lys | Asp | Ser | Arg | Val | Ser | Val | Thr | Lys | Pro | Phe | Met |
| 145 |     |     |     |     | 150 |     |     |     |     | 155 |     |     |     |     | 160 |
| Leu | Pro | Pro | Val | Ala | Ala |
|     |     |     |     |     | 165 |

( 2 ) INFORMATION FOR SEQ ID NO:6:

( i ) SEQUENCE CHARACTERISTICS:
        ( A ) LENGTH: 512 base pairs
        ( B ) TYPE: nucleic acid
        ( C ) STRANDEDNESS: single
        ( D ) TOPOLOGY: linear     ( i i ) MOLECULE TYPE: cDNA     ( x i ) SEQUENCE DESCRIPTION: SEQ ID NO:6:

| | | | | | |
|---|---|---|---|---|---|
| CATATGGAAG | GTATCTGCAG | GAATCGTGTG | ACTGACGATG | TAAAAGACGT | CACTAAATTG | 60 |
| GTGGCAAATC | TTCCAAAAGA | CTACATGATA | ACCCTCAAAT | ATGTCCCCGG | GATGGATGTT | 120 |
| TTGCCAAGTC | ATTGTTGGAT | AAGCGAGATG | GTAGTACAAT | TGTCAGACAG | CTTGACTGAT | 180 |
| CTTCTGGACA | AGTTTTCAAA | TATTTCTGAA | GGCTTGAGTA | ATTATTCCAT | CATAGACAAA | 240 |
| CTTGTGAATA | TAGTGGATGA | CCTTGTGGAG | TGCGTGAAAG | AAAACTCATC | TAAGGATCTA | 300 |
| AAAAAATCAT | TCAAGAGCCC | AGAACCCAGG | CTCTTTACTC | CTGAAGAATT | CTTCCGTATC | 360 |
| TTCAACCGTT | CCATCGACGC | TTTCAAAGAC | TTCGTTGTTG | CTTCCGAAAC | CTCCGACTGC | 420 |
| GTTGTTTCCT | CCACCCTGTC | TCCGGAAAAA | GACTCCCGTG | TTTCGGTTAC | CAAACCGTTC | 480 |
| ATGCTGCCGC | CGGTTGCTGC | TTAATAGGAT | CC | | | 512 |

( 2 ) INFORMATION FOR SEQ ID NO:7:

( i ) SEQUENCE CHARACTERISTICS:
        ( A ) LENGTH: 512 base pairs
        ( B ) TYPE: nucleic acid
        ( C ) STRANDEDNESS: single
        ( D ) TOPOLOGY: linear     ( i i ) MOLECULE TYPE: cDNA     ( x i ) SEQUENCE DESCRIPTION: SEQ ID NO:7:

| | | | | | |
|---|---|---|---|---|---|
| GTATACCTTC | CATAGACGTC | CTTAGCACAC | TGACTGCTAC | ATTTTCTGCA | GTGATTTAAC | 60 |
| CACCGTTTAG | AAGGTTTTCT | GATGTACTAT | TGGGAGTTTA | TACAGGGGCC | CTACCTACAA | 120 |
| AACGGTTCAG | TAACAACCTA | TTCGCTCTAC | CATCATGTTA | ACAGTCTGTC | GAACTGACTA | 180 |
| GAAGACCTGT | TCAAAAGTTT | ATAAAGACTT | CCGAACTCAT | TAATAAGGTA | GTATCTGTTT | 240 |
| GAACACTTAT | ATCACCTACT | GGAACACCTC | ACGCACTTTC | TTTTGAGTAG | ATTCCTAGAT | 300 |
| TTTTTTAGTA | AGTTCTCGGG | TCTTGGGTCC | GAGAAATGAG | GACTTCTTAA | GAAGGCATAG | 360 |
| AAGTTGGCAA | GGTAGCTGCG | AAAGTTTCTG | AAGCAACAAC | GAAGGCTTTG | GAGGCTGACG | 420 |
| CAACAAAGGA | GGTGGGACAG | AGGCCTTTTT | CTGAGGGCAC | AAAGCCAATG | GTTTGGCAAG | 480 |
| TACGACGGCG | GCCAACGACG | AATTATCCTA | GG | | | 512 |

( 2 ) INFORMATION FOR SEQ ID NO:8:

( i ) SEQUENCE CHARACTERISTICS:
        ( A ) LENGTH: 166 amino acids
        ( B ) TYPE: amino acid
        ( C ) STRANDEDNESS: single (D) TOPOLOGY: linear (ii) MOLECULE TYPE: protein (ix) FEATURE:
    (A) NAME/KEY: Protein
    (B) LOCATION: 1..166
    (D) OTHER INFORMATION: /note= "Met sequence starts at -1
        on Sequence No. 8."

(xi) SEQUENCE DESCRIPTION: SEQ ID NO:8:

```
Met Glu Gly Ile Cys Arg Asn Arg Val Thr Asp Asp Val Lys Asp Val
 1               5                  10                  15
Thr Lys Leu Val Ala Asn Leu Pro Lys Asp Tyr Met Ile Thr Leu Lys
             20                  25                  30
Tyr Val Pro Gly Met Asp Val Leu Pro Ser His Cys Trp Ile Ser Glu
         35                  40                  45
Met Val Val Gln Leu Ser Asp Ser Leu Thr Asp Leu Leu Asp Lys Phe
     50                  55                  60
Ser Asn Ile Ser Glu Gly Leu Ser Asn Tyr Ser Ile Ile Asp Lys Leu
65                  70                  75                  80
Val Asn Ile Val Asp Asp Leu Val Glu Cys Val Lys Glu Asn Ser Ser
                 85                  90                  95
Lys Asp Leu Lys Lys Ser Phe Lys Ser Pro Glu Pro Arg Leu Phe Thr
                100                 105                 110
Pro Glu Glu Phe Phe Arg Ile Phe Asn Arg Ser Ile Asp Ala Phe Lys
            115                 120                 125
Asp Phe Val Val Ala Ser Glu Thr Ser Asp Cys Val Val Ser Ser Thr
        130                 135                 140
Leu Ser Pro Glu Lys Asp Ser Arg Val Ser Val Thr Lys Pro Phe Met
145                 150                 155                 160
Leu Pro Pro Val Ala Ala
                165
```

(2) INFORMATION FOR SEQ ID NO:9:

(i) SEQUENCE CHARACTERISTICS:
        (A) LENGTH: 273 amino acids
        (B) TYPE: amino acid
        (C) STRANDEDNESS: single
        (D) TOPOLOGY: linear     (ii) MOLECULE TYPE: protein     (ix) FEATURE:
        (A) NAME/KEY: Protein
        (B) LOCATION: 1..273
        (D) OTHER INFORMATION: /note= "NOTE: Mature full length
            1-248 SCF protein begins at amino acid 26; amino acid
            1-25 include Met and leader sequences for membrane band
            form of human recombinant SCF."

(xi) SEQUENCE DESCRIPTION: SEQ ID NO:9:

```
Met Lys Lys Thr Gln Thr Trp Ile Leu Thr Cys Ile Tyr Leu Gln Leu
 1               5                  10                  15
Leu Leu Phe Asn Pro Leu Val Lys Thr Glu Gly Ile Cys Arg Asn Arg
             20                  25                  30
Val Thr Asn Asn Val Lys Asp Val Thr Lys Leu Val Ala Asn Leu Pro
         35                  40                  45
Lys Asp Tyr Met Ile Thr Leu Lys Tyr Val Pro Gly Met Asp Val Leu
     50                  55                  60
Pro Ser His Cys Trp Ile Ser Glu Met Val Val Gln Leu Ser Asp Ser
65                  70                  75                  80
```

| | | | | | | | | | | | | | | |
|---|---|---|---|---|---|---|---|---|---|---|---|---|---|---|
| Leu | Thr | Asp | Leu | Leu 85 | Asp | Lys | Phe | Ser | Asn 90 | Ile | Ser | Glu | Gly | Leu 95 | Ser |
| Asn | Tyr | Ser | Ile 100 | Ile | Asp | Lys | Leu | Val 105 | Asn | Ile | Val | Asp | Leu 110 | Val |
| Glu | Cys | Val 115 | Lys | Glu | Asn | Ser | Ser 120 | Lys | Asp | Leu | Lys | Ser 125 | Phe | Lys |
| Ser | Pro 130 | Glu | Pro | Arg | Leu | Phe 135 | Thr | Pro | Glu | Glu | Phe 140 | Phe | Arg | Ile | Phe |
| Asn 145 | Arg | Ser | Ile | Asp | Ala 150 | Phe | Lys | Asp | Phe | Val 155 | Val | Ala | Ser | Glu | Thr 160 |
| Ser | Asp | Cys | Val | Val 165 | Ser | Ser | Thr | Leu | Ser 170 | Pro | Glu | Lys | Asp | Ser 175 | Arg |
| Val | Ser | Val | Thr 180 | Lys | Pro | Phe | Met | Leu 185 | Pro | Pro | Val | Ala | Ala 190 | Ser | Ser |
| Leu | Arg | Asn 195 | Asp | Ser | Ser | Ser | Ser 200 | Asn | Arg | Lys | Ala | Lys 205 | Asn | Pro | Pro |
| Gly | Asp 210 | Ser | Ser | Leu | His | Trp 215 | Ala | Ala | Met | Ala | Leu 220 | Pro | Ala | Leu | Phe |
| Ser 225 | Leu | Ile | Ile | Gly | Phe 230 | Ala | Phe | Gly | Ala | Leu 235 | Tyr | Trp | Lys | Lys | Arg 240 |
| Gln | Pro | Ser | Leu | Thr 245 | Arg | Ala | Val | Glu | Asn 250 | Ile | Gln | Ile | Asn | Glu 255 | Glu |
| Asp | Asn | Glu | Ile 260 | Ser | Met | Leu | Gln | Glu 265 | Lys | Glu | Arg | Glu | Phe 270 | Gln | Glu |
| Val | | | | | | | | | | | | | | |

STEM CELL FACTOR ANALOG COMPOSITIONS AND METHOD

FIELD OF THE INVENTION

The present invention relates to stem cell factor ("SCF") analog polypeptide compositions, and vectors, host cells, and processes for recombinant DNA production of the present SCF analogs. Also, in yet other aspects, pharmaceutical compositions, and methods of use are provided.

BACKGROUND

Stem cell factor ("SCF", see PCT Pub. No. WO 91/05795; also called kit-ligand, PCT Pub. No. WO 92/03459, mast cell growth factor, see PCT Pub. WO 92/00376 and Steel factor (or "SF" or "SLF") White, Cell 63: 5–6 (1990)) is hematopoietic factor which acts on hematopoietic progenitor cells. The gene encoding SCF has been cloned and expressed, e.g., Martin, et al., Cell 63: 203–211 (1990), and PCT Pub. No. WO 91/05795, which is herein incorporated by reference in its entirety.

One hallmark of SCF activity is expansion of primitive progenitor cells in the marrow and peripheral blood. Clinically, SCF may prove useful in a number of disease settings where myelosuppression results in significant morbidity and mortality. These settings include the use of SCF in: mobilizing progenitor cells for use in transplantation following myeloablative chemotherapy, priming the marrow before bone-marrow harvest for autologous bone marrow transplantation, and in accelerating hematopoietic reconstitution following standard-dose chemotherapy or myeloablative chemotherapy/total body irradiation.

SCF has numerous active forms, including a membrane bound version and a soluble version. See PCT Pub. No. 91/05795. C-terminal deletion analogs also have activity. For example, SCF 1–137 (with "1" referring to the first amino acid of the mature protein) demonstrates biological activity, and SCF 1–141 demonstrates more or less full biological activity. Langley et al., Arch. Biochem. Biophys. 311: 55–61 (1994). SCF 1–165 having an aspartic acid at position 10, instead of an asparagine as in the native sequence (referred to as "N10D") has also been studied, and found to not appreciably influence the rate of dimer formation. Lu et al., Biochem. J. 305: 563–568 (1995). Certain covalently linked SCF dimers are reported in PCT publication WO 95/26199. Stability is reportedly increased by an intermolecular covalent linkages.

SCF analogs with increased biological activity and stability, such as those provided herein, would be desirable for consumers, as lower dosages may be used to achieve the same biological result. Such analogs would be desirable for producers, as a more active product results in more units of product being sold per production batch. Increased stability, particularly increased shelf-life, would be particularly useful for both consumers and producers. Thus, the present invention provides these advantages and satisfies the needs of consumers and producers.

SUMMARY OF THE INVENTION

Figure 1A:
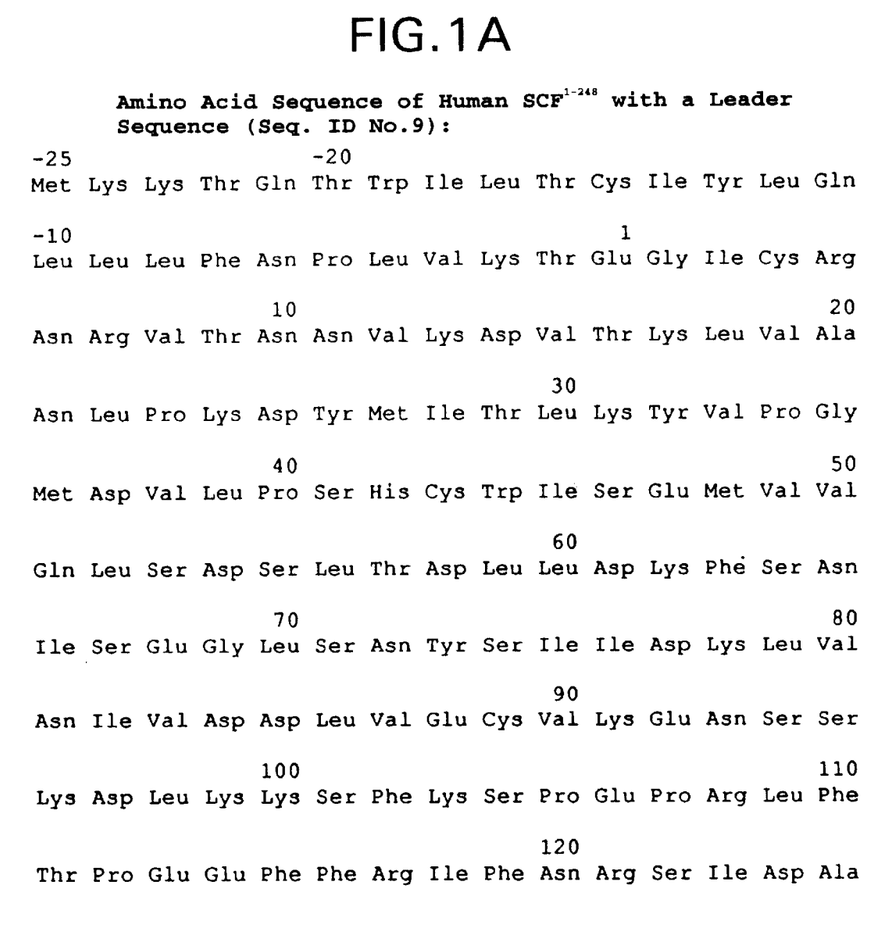
FIG. 1 is an illustration of the amino acid sequence for amino acids 1–248 of the membrane bound form of human recombinant SCF.
Figure 1B:
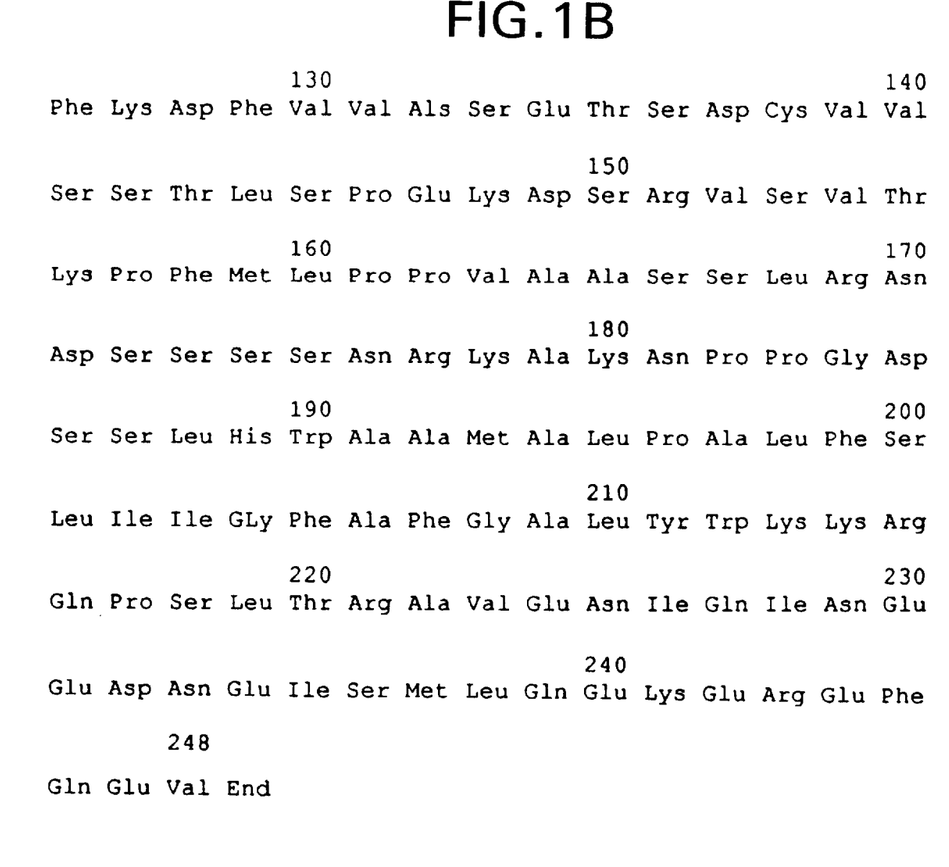

The present invention relates to SCF analogs containing aspartic acid substituted for asparagine at position 10 and position 11 (according to the numbering of FIG. 1, where methionine is at position –1).

Surprisingly, and importantly, it has been found that these substitutions result in SCF analogs having substantially higher biological activity and increased stability as compared to unmodified SCF.

The present analogs resulted in part from observations made during in vitro aging studies, where wild type SCF was found to be highly unstable in certain formulation buffers. Such wild type SCF would be predicted to have shorter shelf life. It has now been found that the major instability of wild type SCF is caused by the deamidation reaction at aspartyl (asparagine, ASN, "N") residue at sequence position 10 (with respect to the mature protein as in FIG. 1). Deamidation also resulted in isomerization of the deamidated aspartyl residue by alpha/beta peptide bond shift. The isomerized SCF species is not biologically active. There is also a risk of antigenicity due to subtle change in the molecular structure. As demonstrated below, the analogs provided herein are more stable than wild type SCF, have increased biological activity, and eliminate any risk associated with deamidation.

Other aspects of the present invention include nucleic acids encoding for the present SCF analogs, vectors, host cells, and processes for recombinant DNA production of the present SCF analogs. Also, in yet other aspects, pharmaceutical compositions, and methods of use are provided.

BRIEF DESCRIPTION OF THE DRAWINGS

FIG. 2 is a graph illustrating the relative amount of intact protein/analog in an accelerated stability assay (see infra). The samples were maintained at 37° C. for 1–5 days, and then analyzed for degradation products. The samples tested were (a) "rhSCF, wild type", recombinant human met-1 SCF 1–165, (b) "N10D, N11D variant", recombinant human met-1 SCF 1–165 having an aspartic acid residue at positions 10 and 11; (c) "N10D variant", i.e., the same as (b), above, except with the aspartic acid at position 10 only; and (d) "N10E variant" the same as N10D except with a glutamic acid at position 10.

DETAILED DESCRIPTION OF THE INVENTION

The present invention relates to particular SCF analogs demonstrating higher biological activity than unmodified SCF. As indicated above, it has been found that substitution of one or both of the asparagines at positions 10 and 11 (according to FIG. 1) results in a molecule demonstrating substantially higher biological activity than unmodified SCF. The present analogs are herein referred to as N10D (for asparagine at the 10th position substituted with asparatic acid) and N10D, N11D (for the SCF analog having an additional substitution at the 11th position). Preferred is N10D, N11D, as changes at both locations result in additional biological activity (in a megakaryocytic cell proliferation assay) over the change N10D alone.

For convenience, the term "N10D " and "N10D, N11D" refer generically to the present SCF analogs, whether analogs of the full length 1–248 SCF protein (FIG. 1) or analogs of some other form as described below. When discussing a particular analog herein, the particular unmodified amino acid sequence is referred to. For example, demonstrated below is SCF analog N10D SCF met 1–165 (an analog of SCF having 165 amino acids of FIG. 1 with an N-terminal methionyl residue, and aspartic acid substituted for asparagine at the 10th position).

The SCF analogs may be analogs as compared to the full length molecule of human SCF (as in FIG. 1) or may be analogs of a modified SCF, such as SCF having amino acids 1–165 or 1–164 of FIG. 1. (The present working examples demonstrate modified SCF 1–165 having a methionyl residue at position –1). Another type of SCF is one having 220 amino acids, due to the deletion of an exon (the membrane bound version of SCF). See, PCT WO 91/05795, entitled, "Stem Cell Factor," published May 2, 1991, herein incorporated by reference in its entirety. The above Stem Cell Factor PCT publication, at FIG. 44, illustrates SCF 1–220. Modified SCFs also include those with deletions of one or more amino acids at the C-terminus, down to amino acids 1–138, or more preferably, 1–141 (of FIG. 1), and those with N-terminal deletions of position 1 through 4 (also of FIG. 1).

Modified SCF may include those having other additions, deletions or substitutions, so long as they possess at least one of the hematopoietic biological activities of naturally occurring human SCF. A preferred hematopoietic biological activity is the ability to stimulate the growth of early hematopoietic progenitor cells. See the SCF PCT publication WO 91/05795, passim. Modification using the present invention of substitution of the asparagine to aspartic acid at the corresponding site on the "starting" SCF molecule is expected to increase the activity of the "starting" SCF molecule. (The term "starting" is quoted because, typically, the nucleic acid encoding these proteins, and not the protein itself, is the starting point for producing the present analogs.)

Specific modified SCFs which may be used as "starting" material to practice the present invention, (as changes corresponding to N10D and N10D, N11D are likely to increase biological activity) include (with reference to FIG. 1):

(a) any of SCF 1–138 or, preferably 1–141 (at least having the C-terminal cysteine of FIG. 1 at that position), through 1–248, as these C-terminal deletions do not appreciably affect biological activity in a UT-7 bioassay (as described below);

(b) SCF 1–127, 1–130 and 1–137, having reduced activity; and (c) any of the above SCFs having N-terminal deletions at the 1, 2, 3, or 4 positions (and having the cysteine remaining at position 4).

In addition, the covalent dimers as reported in WO 95/26199, such as those in which amino acid linkers are used to covalently link the N-terminus of one monomer to the C-terminus of another monomer may include one or more monomer which is an analog of the present invention.

Preferred for "starting" SCFs are SCF 1–248, SCF 1–165, SCF 1–164, as these are thought to possess the greatest biological activity, and have been characterized.

The present SCF analogs may have a methionyl residue at position –1 (typically incident to bacterial expression).

The present SCF analogs may be included in a preparation of monomeric or dimeric forms, and homodimers are preferred for maintaining the highest biological activity. One may have a heterodimer comprised of one N10D and one N10D, N11D molecule, also with heightened activity. One may also prepare a heterodimer with N10D, N11D and native SCF (such as unmodified SCF 1–164 or 1–165). The SCF preparation may be a mixture of hetero- and homodimers, or may be a mixture of such dimers and monomers.

Novel nucleic acid sequences of the invention include sequences useful in securing expression in procaryotic or eucaryotic host cells of the present SCF analogs, N10D and N10D, N11D. The nucleic acids may be purified and isolated, so that the desired coding region is useful to produce the present polypeptides.

More specifically, DNA sequences of the invention comprise:

(a) the DNA sequence set forth in Sequence ID Nos. 3 and 4, and 6 and 7;

(b) the DNA sequences of subpart (a) modified to encode another version of SCF having at least one of the hematopoietic biological properties of naturally occurring human SCF. Preferably the biological property is the property of binding to an SCF receptor (the c-kit receptor), but another biological properties is capability of stimulation of the proliferation of early hematopoietic progenitor cells. Another biological property is capability of stimulation of melanocytes to produce melanin. Other biological properties will be apparent to those skilled in the art.

More specifically, the present nucleic acids are those encoding N10D or N10D, N11D in (with reference to FIG. 1):

(a) any of SCF 1–138 or, preferably 1–141 (at least having the C-terminal cysteine of FIG. 1 at that position), through 1–248;

(b) SCF 1–127, 1–130 and 1–137; and (c) any of the above SCFs having N-terminal deletions at the 1, 2, 3, or 4 positions (and having the cysteine remaining at position 4).

DNA sequences may incorporate codons facilitating transcription and translation of messenger RNA in microbial hosts. Such manufactured sequences may readily be constructed according to the methods of Alton et al., PCT published application WO 83/04053. The DNAs may optionally encode an N-terminal methionyl residue.

DNA sequences provided by the invention are useful in generating new and useful viral and plasmid DNA vectors, new and useful transformed and transfected procaryotic and eucaryotic host cells (including bacterial and yeast cells and mammalian cells grown in culture), and new and useful methods for cultured growth of such host cells capable of expression of the present SCF analogs. The DNA sequences encoding biologically active SCF analogs provided herein (or corresponding RNAs) may be useful for gene therapy in instances where underproduction of SCF would be alleviated.

The present invention also provides for processes for production of the present SCF analogs. Provided is a process for producing SCF analog N10D and/or N10D, N11D, from a host cell containing nucleic acid encoding such SCF analog comprised of:

(a) culturing said host cell containing nucleic acid encoding such SCF analog under conditions facilitating the expression of such DNA molecule; and (b) obtaining such SCF analog. One may optionally purify and isolate such SCF analog from other components obtained in the process.

Host cells may be prokaryotic or eukaryotic and include bacteria, mammalian cells (such as Chinese Hamster Ovary cells, monkey cells, baby hamster kidney cells, or other cells), yeast cells, and insect cells. Preferred for greatest ease in commercial production is production using a bacterial host cell.

Also comprehended by the invention are pharmaceutical compositions comprising effective amounts of polypeptide products of the invention together with pharmaceutically acceptable diluents, preservatives, solubilizers, emulsifiers, adjuvants and/or carriers useful in SCF therapy. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol);

incorporation of the material into particulate preparations of polymeric compounds such as polylactic acid, polyglycolic acid, etc. or in association with liposomes. Such compositions will influence the physical state, stability, rate of in vivo release, and rate of in vivo clearance of the present SCF analogs. See, e.g., Remington's Pharmaceutical Sciences, 18th Ed. (1990, Mack Publishing Co., Easton, Pa. 18042) pages 1435–1712 which are herein incorporated by reference.

Derivatives of the present SCF analogs are also comprehended herein. Such derivatives include molecules modified by one or more water soluble polymer molecules, such as polyethylene glycol, or by the addition of polyamino acids. Such derivatization may occur singularly at the N- or C-terminus or there may be multiple sites of derivatization. Substitution of one or more amino acids with lysine may provide additional sites for derivatization.

The present analogs or derivatives thereof may be formulated for injection, or oral, nasal, pulmonary, topical, or other types of administration as one skilled in the art will recognize. The formulation may be liquid or may be solid, such as lyophilized, for reconstitution.

In general, the present analogs (or derivatives thereof) will be useful in the same way that currently available SCFs are useful, except the present analogs provide for greater efficacy (approximately 200% as will be demonstrated below). These uses include the treatment of a variety of hematopoietic, neurological and reproduction related conditions. See WO 91/05795 which has been incorporated by reference, see also U.S. Ser. No. 07/982,255 which is also herein incorporated by reference. Thus, the present compositions and methods for manufacture of medicaments may be useful for the treatment of such conditions. Such conditions include but are not limited to the treatment of leucopenia, the treatment of thrombocytopenia, the treatment of anemia, enhancing engraftment of bone marrow during transplantation, enhancing bone marrow recovery in treatment of radiation, chemical or chemotherapeutic induced bone marrow aplasia or myelosuppression, acquired immune deficiency syndrome, and sensitizing cells to chemotherapy. In addition, the present SCF analog compositions may be used for mobilization of peripheral blood progenitor cells. Such uses and compositions also include providing treatment to a mammal suffering from nerve damage, infertility, or intestinal damage. In addition, the present SCF analog compositions may be useful for the treatment of pigmentation disorders, such as vitilago.

The present SCF analog (or derivative) compositions may also be used in vitro. For example, in a gene therapy setting, one may desire to transfect a hematopoietic cell with exogenous DNA, and culture said cell using the present SCF analog formulations. Thus, in yet another aspect the present invention involves a method for culturing hematopoietic cells in vitro comprised of:
  (i) placing said cells in a suitable culture medium, said suitable culture medium containing an SCF analog composition according to the present invention, and
  (ii) providing suitable conditions for the growth of said hematopoietic cells.

More particularly, the present invention provides a method of transfecting hematopoietic cells with exogenous DNA comprising:
  (i) culturing said hematopoietic cells with an SCF analog composition according to the present invention, and
  (ii) transfecting said cultured cell with exogenous DNA. The hematopoietic cells may be, for example, bone marrow cells or peripheral blood progenitor cells.

In yet another aspect, the present invention provides a kit containing components for culturing bone marrow cells or peripheral blood progenitor cells comprised of:
  (i) an SCF analog composition of the present invention; and
  (ii) components suitable for preparing medium for culturing bone marrow cells or peripheral blood progenitor cells.

The uses or products herein may involve the administration or inclusion of at least one additional factor selected from among EPO, G-CSF, M-GDF, GM-CSF, M-CSF, CSF-1, IL-1, IL-2, IL-3, IL-4, IL-5, IL-6, IL-7, IL-8, IL-9, IL-10, IL-11, IL-12, IGF-1, LIF, interferon (such as $\alpha$, $\beta$, gamma or consensus) neurotrophic factors (such as BDNF, NT-3, CTNF or noggin), other multi-potent growth factors (such as, to the extent these are demonstrated to be such multi-potent growth factor, flt-3/flk-2 ligand, stem cell proliferation factor, and totipotent stem cell factor), fibroblast growth factors (such as FGF), and analogs, fusion molecules or other derivatives of the above. For example, SCF in combination with G-CSF has been found to mobilize peripheral blood progenitor cells in vivo. Ex vivo, for example, SCF in combination with G-CSF, IL-3 and IL-6 has been found useful for expansion of peripheral blood cells. The present analogs will provide for similar uses.

Generally, an effective amount of the present SCF analogs (or derivatives) will be determined by the age, weight and condition or severity of disease of the recipient. See, Remingtons Pharmaceutical Sciences, supra, at pages 697–773, herein incorporated by reference. Typically, a dosage of between about 0.001 $\mu$g/kg body weight/day to about 1000 $\mu$g/kg body weight/day, may be used, but more or less, as a skilled practitioner will recognize, may be used. Dosing may be one or more times daily, or less frequently, and may be in conjunction with other compositions as described herein. It should be noted that the present invention is not limited to the dosages recited herein.

The following example are offered to more fully illustrate the invention, but are not to be construed as limiting the scope thereof. The example illustrates the preparation of the present SCF met 1–165 N10D and N10D, N11D, and the determination that avoiding deamidation at the asparagine at the 10th and/or 11th position avoids degradation by-products of recombinant human SCF. The testing of these SCF analogs in vitro is also described.

EXAMPLES

1. Determination that the asparagine residue at positions 10 and/or 11 influences the biological function and chemical stability of recombinant human SCF.

During in vitro aging, deamidation of recombinant human stem cell factor (rhSCF1–165) was detected by HPLC analysis and by release of soluble ammonia. Deamidation rate is slow in buffers at a low pH or at low temperatures, but the rate is significantly accelerated in alkaline buffers such as sodium bicarbonate in combination with elevated temperatures. HPLC isolation of various deamidated forms followed by peptide map analysis revealed that the deamidation involved asparagine at the 10th position in protein. Following peptide mapping analysis, significant amounts of aspartyl and isoaspartyl peptides were identified, indicating the conversion of the asparagine at position 10 into both aspartate and isoaspartate residues. As a result of spontaneous association-dissociation of the rhSCF dimer (see, Lu et al., Biochem J. 305: 563–568 (1995)), a total of five deamidated forms, including two homodimers and three heterodimers, were detected and isolated. Cell proliferation assays showed that two rhSCF heterodimeric species, derived from dimerization between isoaspartyl rhSCF and other rhSCF monomers, retain only approximately half of the biological activity. The homodimer with isoaspartic acid in place of asparagine is 50-fold less potent, while the aspartyl homodimer, either isolated during deamidation experiments or recombinantly prepared by site-directed mutagenesis as described above, had higher activity than the standard molecule. In comparison, synthetic N10A (having an alanine at the 10th position) or N10E (having a glutamic acid at the 10th position), though missing the deamidation site, were significantly less active. All these analogs were relatively more stable than those containing the asparagine residue. These results indicated that the biological function and the chemical stability of recombinant human SCF are influenced by the nature of the residue at position 10.

2. Preparation of SCF met 1–165 N10D, and N10D, N11D

In view of the above studies demonstrating that deamidation at position 10 resulted in loss of activity and instability of rhSCF preparations, the present N10D and N10D, N11D analogs were prepared and tested for biological activity and stability.

The present SCF analogs were prepared by site-directed mutagenesis of SCF met 1–165. The *E. coli* expression of SCF met 1–165 was previously reported. Langley et al., Arch. Biochem. Biophys. 295: 21–28 (1992). The DNA encoding recombinant human SCF had an initial methionine codon followed by codons for human SCF 1–165. The purified recombinant human SCF retains the initiating Met (position Met -1). The present N10D and N10D, N11D analogs were prepared by site-directed mutagenesis as described in Langley et al., Arch. Biochem. Biophys. 311: 55–61 (1994). Other "test" analogs, N10A and N10E, were also prepared in this fashion.

The amino acid sequence and nucleic acid sequence for SCF met 1–165 was (Seq. ID Nos. 1 (DNA) and 2 (amino acid)):

```
ATGGAAGGTA  TCTGCCGTAA  CCGTGTTACT  AACAACGTTA  AAGACGTTAC
 M  E  G     I  C  R  N   R  V  T    N  N  V     K  D  V  T

TAAACTGGTT  GCTAACCTGC  CGAAAGACTA  CATGATCACC  CTGAAATACG
 K  L  V    A  N  L  P   K  D  Y     M  I  T    L  K  Y

TTCCGGGTAT  GGACGTTCTG  CCGTCTCACT  GCTGGATCTC  TGAAATGGTT
 V  P  G  M  D  V  L     P  S  H    C  W  I  S   E  M  V

GTTCAGCTGT  CTGACTCTCT  GACTGACCTG  CTGGACAAAT  TCTCTAACAT
 V  Q  L    S  D  S  L   T  D  L    L  D  K     F  S  N  I

CTCTGAAGGT  CTGTCTAACT  ACTCTATCAT  CGACAAACTG  GTTAACATCG
 S  E  G     L  S  N    Y  S  I  I   D  K  L    V  N  I

TTGACGACCT  GGTTGAATGC  GTTAAAGAAA  ACTCTTCTAA  AGACCTGAAA
 V  D  D  L  V  E  C    V  K  E     N  S  S  K   D  L  K

AAATCTTTCA  AATCTCCGGA  ACCGCGTCTG  TTCACTCCGG  AAGAATTCTT
 K  S  F    K  S  P  E   P  R  L    F  T  P     E  E  F  F

CCGTATCTTC  AACCGTTCCA  TCGACGCTTT  CAAAGACTTC  GTTGTTGCTT
 R  I  F    N  R  S     I  D  A  F   K  D  F    V  V  A

CCGAAACCTC  CGACTGCGTT  GTTTCCTCCA  CCCTGTCTCC  GGAAAAAGAC
 S  E  T  S  D  C       V  V  S  S   T  L  S  P  E  K  D

TCCCGTGTTT  CGGTTACCAA  ACCGTTCATG  CTGCCGCCGG  TTGCTGCTTAA
 S  R  V    S  V  T  K   P  F  M    L  P  P    V  A  A  *
```

45

The amino acid sequence and nucleic acid sequence for SCF met 1–165 N10D was (Seq. ID Nos. 3 and 4 (DNA) and 5 (amino acid)):

```
    CATATGGAAGGTATCTGCAGGAATCGTGTGACTGACAATGTAAAAGACGTCACTAAATTG
1   ---------+---------+---------+---------+---------+---------+   60
    GTATACCTTCCATAGACGTCCTTAGCACACTGACTGTTACATTTTCTGCAGTGATTTAAC
       M  E  G  I  C  R  N  R  V  T  D  N  V  K  D  V  T  K  L   -

GTGGCAAATCTTCCAAAAGACTACATGATAACCCTCAAATATGTCCCCGGGATGGATGTT
61  ---------+---------+---------+---------+---------+---------+  120
    CACCGTTTAGAAGGTTTTCTGATGTACTATTGGGAGTTTATACAGGGGCCCTACCTACAA
       V  A  N  L  P  K  D  Y  M  I  T  L  K  Y  V  P  G  M  D  V  -

TTGCCAAGTCATTGTTGGATAAGCGAGATGGTAGTACAATGGTCAGACAGCTTGACTGAT
121 ---------+---------+---------+---------+---------+---------+  180
    AACGGTTCAGTAACAACCTATTCGCTCTACCATCATGTTAACAGTCTGTCGAACTGACTA
       L  P  S  H  C  W  I  S  E  M  V  V  Q  L  S  D  S  L  T  D  -

CTTCTGGACAAGTTTTCAAATATTTCTGAAGGCTTGAGTAATTATTCCATCATAGACAAA
181 ---------+---------+---------+---------+---------+---------+  240
    GAAGACCTGTTCAAAAGTTTATAAAGACTTCCGAACTCATTAATAAGGTAGTATCTGTTT
       L  L  D  K  F  S  N  I  S  E  G  L  S  N  Y  S  I  I  D  K  -
```

```
     CTTGTGAATATAGTGGATGACCTTGTGGAGTGCGTGAAAGAAAACTCATCTAAGGATCTA
241  ---------+---------+---------+---------+---------+---------+  300
     GAACACTTATATCACCTACTGGAACACCTCACGCACTTTCTTTTGAGTAGATTCCTAGAT
        L   V   N   I   V   D   D   L   V   E   C   V   K   E   N   S   S   K   D   L    -

AAAAAATCATTCAAGAGCCCAGAACCCAGGCTCTTTACTCCTGAAGAATTCTTCCGTATC
301  ---------+---------+---------+---------+---------+---------+  360
     TTTTTTAGTAAGTTCTCGGGTCTTGGGTCCGAGAAATGAGGACTTCTTAAGAAGGCATAG
        K   K   S   F   K   S   P   E   P   R   L   F   T   P   E   E   F   F   R   I    -

TTCAACCGTTCCATCGACGCTTTCAAAGACTTCGTTGTTGCTTCCGAAACCTCCGACTGC
361  ---------+---------+---------+---------+---------+---------+  420
     AAGTTGGCAAGGTAGCTGCGAAAGTTTCTGAAGCAACAACGAAGGCTTTGGAGGCTGACG
        F   N   R   S   I   D   A   F   K   D   F   V   V   A   S   E   T   S   D   C    -

GTTGTTTCCTCCACCCTGTCTCCGGAAAAAGACTCCCGTGTTTCGGTTACCAAACCGTTC
421  ---------+---------+---------+---------+---------+---------+  480
     CAACAAAGGAGGTGGGACAGAGGCCTTTTTCTGAGGGCACAAAGCCAATGGTTTGGCAAG
        V   V   S   S   T   L   S   P   E   K   D   S   R   V   S   V   T   K   P   F    -

ATGCTGCCGCCGGTTGCTGCTTAATAGGATCC
481  ---------+---------+---------+--- 512
     TACGACGGCGGCCAACGACGAATTATCCTAGG
        M   L   P   P   V   A   A   *   *
```

The amino acid sequence and nucleic acid sequence for SCF met 1–165 N10D, N11D was (Seq. ID Nos. 6 and 7 (DNA) and 8 (amino acid)):

```
     CATATGGAAGGTATCTGCAGGAATCGTGTGACTGACGATGTAAAAGACGTCACTAAATTG
1    ---------+---------+---------+---------+---------+---------+  60
     GTATACCTTCCATAGACGTCCTTAGCACACTGACTGCTACATTTTCTGCAGTGATTTAAC
        M   E   G   I   C   R   N   R   V   T   D   D   V   K   D   V   T   K   L    -

GTGGCAAATCTTCCAAAAGACTACATGATAACCCTCAAATATGTCCCCGGGATGGATGTT
61   ---------+---------+---------+---------+---------+---------+  120
     CACCGTTTAGAAGGTTTTCTGATGTACTATTGGGAGTTTATACAGGGGCCCTACCTACAA
        V   A   N   L   P   K   D   Y   M   I   T   L   K   Y   V   P   G   M   D   V    -

TTGCCAAGTCATTGTTGGATAAGCGAGATGGTAGTACAATTGTCAGACAGCTTGACTGAT
121  ---------+---------+---------+---------+---------+---------+  180
     AACGGTTCAGTAACAACCTATTCGCTCTACCATCATGTTAACAGTCTGTCGAACTGACTA
        L   P   S   H   C   W   I   S   E   M   V   V   Q   L   S   D   S   L   T   D    -

CTTCTGGACAAGTTTTCAAATATTTCTGAAGGCTTGAGTAATTATTCCATCATAGACAAA
181  ---------+---------+---------+---------+---------+---------+  240
     GAAGACCTGTTCAAAAGTTTATAAAGACTTCCGAACTCATTAATAAGGTAGTATCTGTTT
        L   L   D   K   F   S   N   I   S   E   G   L   S   N   Y   S   I   I   D   K    -

CTTGTGAATATAGTGGATGACCTTGTGGAGTGCGTGAAAGAAAACTCATCTAAGGATCTA
241  ---------+---------+---------+---------+---------+---------+  300
     GAACACTTATATCACCTACTGGAACACCTCACGCACTTTCTTTTGAGTAGATTCCTAGAT
        L   V   N   I   V   D   D   L   V   E   C   V   K   E   N   S   S   K   D   L    -

AAAAAATCATTCAAGAGCCCAGAACCCAGGCTCTTTACTCCTGAAGAATTCTTCCGTATC
301  ---------+---------+---------+---------+---------+---------+  360
     TTTTTTAGTAAGTTCTCGGGTCTTGGGTCCGAGAAATGAGGACTTCTTAAGAAGGCATAG
        K   K   S   F   K   S   P   E   P   R   L   F   T   P   E   E   F   F   R   I    -

TTCAACCGTTCCATCGACGCTTTCAAAGACTTCGTTGTTGCTTCCGAAACCTCCGACTGC
361  ---------+---------+---------+---------+---------+---------+  420
     AAGTTGGCAAGGTAGCTGCGAAAGTTTCTGAAGCAACAACGAAGGCTTTGGAGGCTGACG
        F   N   R   S   I   D   A   F   K   D   F   V   V   A   S   E   T   S   D   C    -

GTTGTTTCCTCCACCCTGTCTCCGGAAAAAGACTCCCGTGTTTCGGTTACCAAACCGTTC
421  ---------+---------+---------+---------+---------+---------+  480
     CAACAAAGGAGGTGGGACAGAGGCCTTTTTCTGAGGGCACAAAGCCAATGGTTTGGCAAG
        V   V   S   S   T   L   S   P   E   K   D   S   R   V   S   V   T   K   P   F    -

ATGCTGCCGCCGGTTGCTGCTTAATAGGATCC
481  ---------+---------+---------+--- 512
     TACGACGGCGGCCAACGACGAATTATCCTAGG
        M   L   P   P   V   A   A   *   *
```

Characterization

Confirmation of the identity of SCF met 1–165 N10D and N10D, N11D was accomplished by N-terminal amino acid sequence of intact proteins. Amino acid sequence of SCF N10D was determined to be Met-Glu-Gly-Ile-[Cys]-Arg-Asn-Arg-Val-Thr-Asp-Asn-Val-Lys---, (amino acid residues 1–14 of SEQ ID NO:5), while the sequence of SCF N10D, N11D was elucidated to be Met-Glu-Gly-Ile-[Cys]-Arg-Asn-Arg-Val-Thr-Asp-Asp-Val-Lys---- (amino acid residues 1–14 of SEQ ID NO:8). Therefore the determined sequences of both purified SCF N10D and SCF N10D, N11D match the sequences predicted from the respective DNA sequences shown in SEQ ID nos. 3 and 4 and SEQ ID nos. 6 and 7.

3. Increased Biological Activity. Presented below are data demonstrating that the present recombinant human SCF analogs N10D and N10D, N11D are approximately 50% more biologically active than the non-modified recombinant human SCF 1–165.

Biological Activity Assay

An in vitro UT-7 bioassay was performed by measuring the stimulatory effect of SCF on the proliferation of megakaryocytic cell culture. The $^3$H-thymidine uptake of the cultured cells stimulated by the samples are indicative of biological potency for SCF. Methods used were according to Smith et al., in Current Protocols in Immunology (Coligan, et al., eds.) pp. 6.17.1 to 6.17.11, John Wiley & Sons, New York.

Results comparing the present analogs to unmodified SCF met 1–165 are presented below:

| Sample | Half Maximal stimulation concentration (ng/ml) | % activity[1] |
|---|---|---|
| SCF met 1-165 | 5.4 | 100 |
| SCF met 1-165 N10D | 3.5 | 154 |
| SCF met 1-165 N10D, N11D | 3.2 | 160 |

[1]This was determined using the half maximal stimulation concentration for standard recombinant human SCF (5.4), divided by the value for the variant (3.5 or 3.2) and multiplied by 100.

These results demonstrate that in vitro, the biological activity of the present recombinant human SCF1–165 N10D and N10D, N11D analogs is approximately 50% higher than native recombinant human SCF1–165.

4. Increased stability. Presented below are data demonstrating that the present recombinant human SCF1–165 analogs are more stable in accelerated stability assays than non-modified recombinant human SCF1–165.

Figure 2:
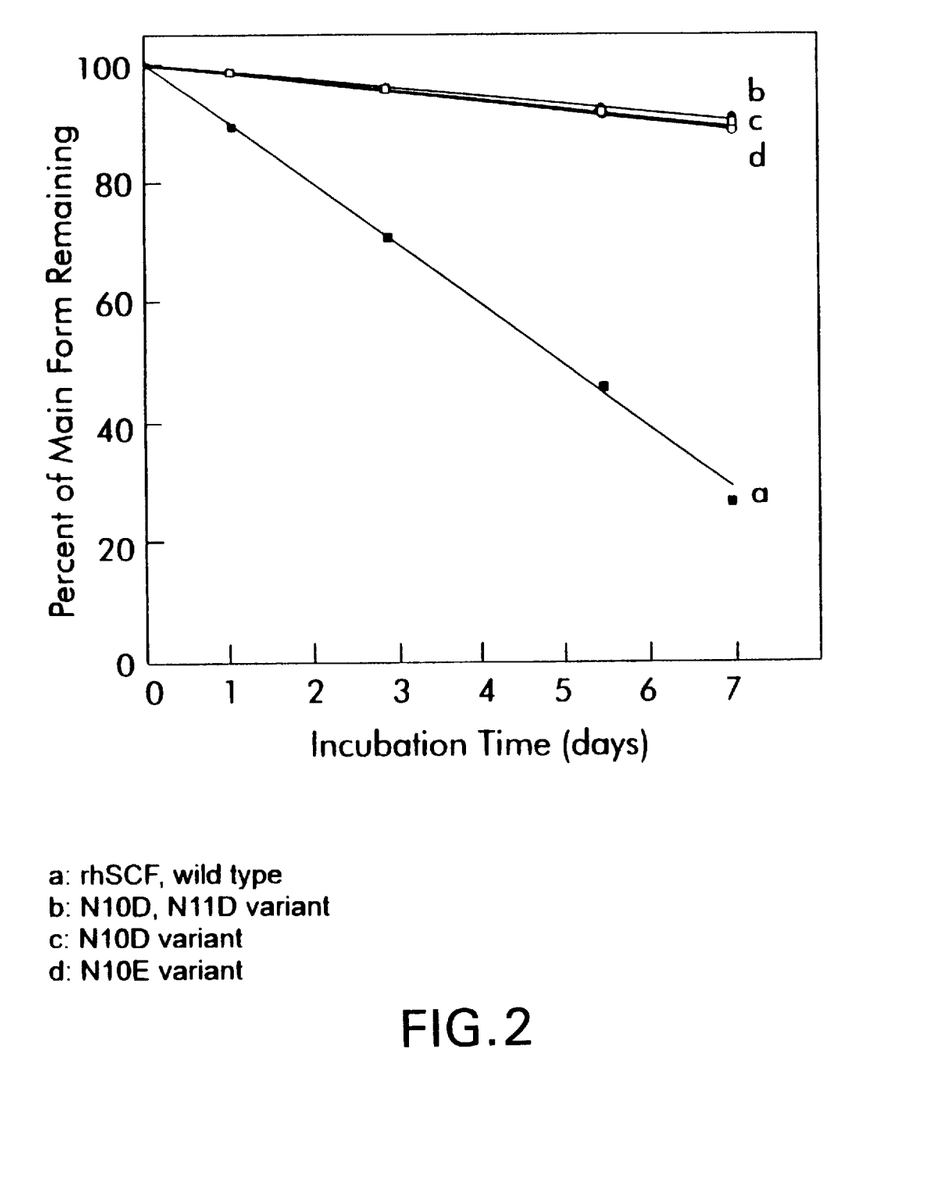

Stability assays. Comparative accelerated stability among SCF, SCF N10D and SCF N10D, N11D was evaluated by incubating samples in 100 mM sodium bicarbonate, pH 8.4 at 37° C. for 1–5 days. Sulfopropyl cationic exchange HPLC using SP-5PW TSK gel columns was performed to quantify the amount of the remaining undegraded form and the deamidation products formed upon storage in the above mentioned buffer. As indicated in FIG. 2, SCF N10D and SCF N10D, N11D are equally as stable during incubation and exhibit better stability than the standard SCF.

While the present invention has been described in terms of preferred embodiments, it is understood that variations and modifications will occur to those skilled in the art. Therefore, it is intended that the appended claims cover all such equivalent variations which come within the scope of the invention as claimed.

What is claimed is:

1. A stem cell factor analog, wherein said analog has the amino acid SEQ ID NO:8.

2. A stem cell factor analog, wherein said analog is selected from the group consisting of:

(a) any of stem cell factor having amino acid residues 26–163 through 26–273 of SEQ ID NO: 9, wherein each of the Asn residues at positions 35 and 36 of SEQ ID NO:9 are replaced with an Asp residue;

(b) stem cell factor having amino acid residues 26–152, 26–155, or 26–162 of SEQ ID NO:9, wherein each of the Asn residues at positions 35 and 36 of SEQ ID NO:9 are replaced with an Asp residue;

(c) any of the stem cell factors of subparts (a) or (b) having N-terminal deletions at the 26, 27, or 28 positions of SEQ ID NO:9 and having the cysteine remaining at position 29 of SEQ ID NO:9; and (d) any of the stem cell factors of subparts (a), (b), or (c) having an N-terminal methionyl residue.

3. A composition comprising a stem cell factor analog of claim 1 or 2 and a pharmaceutically acceptable diluent, adjuvant, or carrier.

* * * * *

UNITED STATES PATENT AND TRADEMARK OFFICE
CERTIFICATE OF CORRECTION

PATENT NO. : 5,885,962
DATED : March 23, 1999
INVENTOR(S) : Hsieng Lu

It is certified that error appears in the above-identified patent and that said Letters Patent is hereby corrected as shown below:

Column 4,
Line 6, change to "properties" to -- property --

Column 6,
Line 38, change "example" to -- examples --
Line 40, change "example illustrates" to -- examples illustrate --

Column 8,
Sequence ID No. 3, change character 161 "G" to -- T --

Column 11,
Line 6, change "Lys---" to -- Lys---- --

Signed and Sealed this

Fifteenth Day of January, 2002

Attest:

JAMES E. ROGAN
Director of the United States Patent and Trademark Office

Attesting Officer